United States Patent [19]

Mitsuhashi et al.

[11] Patent Number: 5,019,385

[45] Date of Patent: May 28, 1991

[54] NOVEL LYMPHOPINE LK 2 AND PHARMACEUTIC COMPOSITIONS CONTAINING SAME

[75] Inventors: Masakazu Mitsuhashi; Masashi Kurimoto, both of Okayama, Japan

[73] Assignee: Kabushiki Kaisha Hayashibara Seibutsu Kagaku Kenkyujo, Okayama, Japan

[21] Appl. No.: 792,158

[22] Filed: Oct. 28, 1985

[30] Foreign Application Priority Data

| | | |
|---|---|---|
| Nov. 9, 1984 [JP] | Japan | 59-236356 |
| Nov. 9, 1984 [JP] | Japan | 59-236357 |
| Feb. 18, 1985 [JP] | Japan | 60-28396 |
| Jul. 30, 1985 [JP] | Japan | 60-166754 |

[51] Int. Cl.$^5$ ............................................. C07K 15/12
[52] U.S. Cl. ........................................ 424/85; 530/351; 514/2; 514/8
[58] Field of Search .............. 530/351; 424/85; 514/2, 514/8

[56] References Cited

U.S. PATENT DOCUMENTS

| | | | |
|---|---|---|---|
| 4,276,282 | 6/1981 | Sugimoto et al. | 424/85 |
| 4,285,929 | 8/1981 | Sugimoto et al. | 424/85 |
| 4,481,137 | 11/1984 | Ohnishi et al. | 260/112 |
| 4,758,549 | 7/1988 | Mitsuhashi et al. | 514/8 |

FOREIGN PATENT DOCUMENTS

| | | |
|---|---|---|
| 0064401 | 4/1982 | European Pat. Off. . |
| 0092163 | 4/1983 | European Pat. Off. . |
| 0102601 | 8/1983 | European Pat. Off. . |
| 0111344 | 12/1983 | European Pat. Off. . |
| 0133551 | 8/1984 | European Pat. Off. . |
| 8500830 | 2/1985 | PCT Int'l Appl. . |
| 2153364 | 8/1985 | United Kingdom . |

OTHER PUBLICATIONS

Zoon, K. Methods in Enzymology, 78, pp. 457–464, 1981.
Chadha, K. C. Methods in Enzymology, 78, pp. 220–226, 1981.
British Search Report.

*Primary Examiner*—Christine Nucker
*Attorney, Agent, or Firm*—Browdy and Neimark

[57] ABSTRACT

A novel lymphokine, the monoclonal antibody specific to the lymphokine, and their production and uses are disclosed. The lymphokine is a glycoprotein with a molecular weight of 20,000±2,000 daltons; isoelectric point pI, 6.2±0.3; electrophoretic mobility Rf, 0.29±0.02; cytotoxic on L 929 cell; and substantially not growth-inhibitive on KB cell. The lymphokine significantly inhibits the growth of malignant human tumors in vivo. The monoclonal antibody is of IgM or IgG class, and neutralizes specifically the cytotoxic activity of the lymphokine. Combined use of LK 2 with chemotherapeutic such as alkylating agents, metabolic antagonists, antioncotic antibiotics and plant alkaloids enhances greatly the antioncotic effect of the chemotherapeutics.

26 Claims, No Drawings

NOVEL LYMPHOPINE LK 2 AND PHARMACEUTIC COMPOSITIONS CONTAINING SAME

FIELD OF THE INVENTION

The present invention relates to a monoclonal antibody specific to a novel lymphokine, and the production thereof.

BACKGROUND OF THE INVENTION

Lymphotoxin (LT) and tumor necrosis factor (TNF) are known as lymphokines which damage tumor cells. For example, LT is described in Aoki, Ryuichi et al., *SHIN-MENEKIGAKU SOSHO*, Vol. 6, "Lymphokine", pp. 87–105 (1979), published by Igaku-Shoin, Tokyo, *In Vitro Method in Cell-Mediated Immunity*, edited by Bloom, B. R. & Glade, P. R., published by Academic Press, Inc. (1971), and *Cellular Immunology*, Vol. 38, pp. 388–402 (1978); and TNF is described in Carswell, E. A. et al., *Proceedings of the National Academy of Sciences of the U.S.A.*, Vol. 72, No. 9, pp. 3,666–3,670 (1975), and *Lymphokines*, Vol. 2, pp. 235–272, "Tumor Necrosis Factor", edited by Pick, E., published by Academic Press, Inc. (1981).

Recently, Ohnishi, H. et al. disclosed an antioncotic lymphokine glycoprotein in Japan Patent Kokai No. 146,293/83.

Milstein, C. reviewed monoclonal antibodies in *Scientific American*, Vol. 243, No. 4, pp. 56–64 (1980).

In chemotherapeutics, generally one or more alkylating agents, metabolic antagonists, antioncotic antibiotics, and plant alkaloids are used.

Chemotherapeutics, however, have the disadvantages that their use may cause excessive side-effects in patients; that their tumor spectra are relatively narrow and insufficient; and that they are liable to induce drug-resistant tumors.

DETAILED DESCRIPTION OF THE INVENTION

In view of the foregoing, the present inventors have studied lymphokines over a period of years. As the result, they have discovered a novel lymphokine with physicochemical properties entirely different from those of known lymphokines, and having cytotoxic activity on malignant tumor cells. Thus, they have established the production and uses of the lymphokine, in addition to the monoclonal antibody specific to the lymphokine and its production.

More particularly, the present invention relates to a novel lymphokine possessing the following physicochemical properties:

(1) Molecular weight:
20,000±2,000 daltons;
(2) Isoelectric point:
pI=6.2±03;
(3) Electrophoretic mobility:
on Disc-PAGE, Rf=0.29±0.02;
(4) uv-Absorption spectrum:
an absorption maximum at a wave length of about 280 nm;
(5) Solubility in solvents:
soluble in water, saline and phosphate buffer, scarcely soluble or insoluble in ethyl ether, ethyl acetate or chloroform;
(6) Coloring reaction:
protein-positive by Lowry's method or the microburet method,
saccharide-positive by the phenol-sulfuric acid method or anthrone-sulfuric acid method;
(7) Biological activities:
cytotoxic on L 929 cell,
substantially not growth-inhibitive on KB cell
substantially free of interferon activity;
(8) Stability in aqueous solution:
stable up to 60° C. when incubated at pH 7.2 for 30 minutes,
stable in the pH range of 4.0–11.0 when incubated at 4° C. for 16 hours; and
(9) Stability on cryopreservation:
stable at −10° C. over a period of one month or longer.

The present invention also relates to the production and uses of the lymphokine, as well as to the monoclonal antibody specific to the lymphokine and production thereof.

The novel lymphokine in accordance with the present invention will be abbreviated simply as "LK 2" hereinafter.

LK 2 is produced by exposing an LK 2 producing human cell, e.g., human leukocytes, human lymphocytes or established cell lines thereof, to an LK 2 inducer. Human leukocytes and lymphocytes can be isolated from fresh human blood. The established human cell line can be proliferated with conventional in vitro methods.

For a more efficient practice of the present invention, it is desirable to employ an in vivo cell proliferation procedure wherein such the human cell line is transplanted directly in to a non-human warm-blooded animal, or, alternatively, inoculated in a conventional-type diffusion chamber by which the nutrient body fluid of a non-human warm-blooded animal is supplied to the cell line.

Unlike in vitro cell proliferation, the in vivo procedure requires no or much less nutrient medium containing expensive serum, the cell proliferation is much easier, and the proliferated human cells give a much higher LK 2 activity.

In addition, in the in vivo procedure the human cell line can be easily proliferated while utilizing the nutrient body fluid supplied from a non-human warm-blooded animal by transplanting the human cell line to the non-human warm-blooded animal, or, alternatively, placing the cell line in a conventional-type diffusion chamber devised to receive the body fluid, and embedding or placing the chamber in or on the animal. In either case, the animals are fed in the usual way.

Furthermore, the in vivo procedure has the additional features of a much more stabilized and rapid cell proliferation, a higher cell production, and an extremely higher LK 2 production per cell, as compared with the in vitro procedure.

The human cell lines usable in the present invention may be those which are LK 2-producible, transplantable to a non-human warm-blooded animal, and readily proliferatable in the animal. For example, a variety of human cell lines listed in *Protein, Nucleic Acid and Enzyme*, Vol. 20, No. 6, pp. 616–643 (1975) are employable in the invention. Specifically suited are human lymphoblastoid lines, such as Namalwa (ATCC CRL 1432), as described in *Journal of Clinical Microbiology*, Vol. 1, pp. 116–117 (1975); BALL-1, TALL-1 and NALL-1, as described by Miyoshi, I., *Nature*, Vol. 267, pp. 843–844

(1977); M-7002 and B-7101, as described in *The Journal of Immunology*, Vol. 113, pp. 1,334–1,345 (1974); JBL, EBV-Sa, EBV-Wa, MOLT-3 (ATCC CRL 1552) and EBV-HO, as described in *The Tissue Culture*, Vol. 6, No. 13, pp. 527–546 (1980); CCRF-SB (ATCC CCL 120); CCRF-CEM (ATCC CCL 119); BALM 2; DND-41; and other established cell lines obtained by transforming normal human monocyte or granulocyte cells with any carcinogenic virus, agent or radiation.

The proliferation rate and/or LK 2 productivity per cell of these cell lines may be improved by cell fusion techniques using polyethylene glycol or Sendai virus, or by gene recombinant techniques using nuclease enzyme, ligase enzyme, DNA polymerase enzyme, etc. The listing of the employable human cell lines in the present specification is not intended in any way to limit the scope of the invention. One or more members of these cell lines may be used in combination in the steps up to the LK 2 induction which will be described hereinafter. If necessary, human leukocytes or lymphocytes, which can be prepared from fresh human blood, may be used in combination with any of the human cell lines.

The non-human warm-blooded animal usable in the invention may be any one of those in which such human cells are proliferatable. Examples of such animals are fowl, such as chicken and pigeon; and mammals, such as dog, cat, monkey, rabbit, goat, pig, horse, cow, guinea pig, rat, nude rat, hamster, mouse, nude mouse, etc.

Since transplantation of the human cells to the animal can eliciton undesirable immunoreaction, the use of a non-human warm-blooded animal in the youngest possible stage, e.g., egg, embryo or foetus, or newborn or infant animal, is desirable in order to reduce such immunoreaction as far as possible.

Prior to the transplantation, the animal may be irradiated with x-ray or $\gamma$-ray, about 200–600 rem, or injected with a antiserum or an immunosuppressant to reduce the immunoreaction to the lowest possible level.

When an immunodeficient animal, such as nude mouse and nude rat, is used as the host animal, any of the aforementioned human cell lines can be transplanted into these animals without such pretreatment, and proliferated readily with less fear of causing undesirable immunoreaction because these animals exhibit less immunoreaction even in their adulthood.

One can stabilize cell proliferation and/or augment LK 2 production by successive transplantation using the same or different non-human warm-blooded animals. These objectives can be attained, for example, by first transplanting a human cell line to a hamster and proliferating the human cell in the hamster, then successively transplanting the proliferated human cell to a nude mouse. In this case, the successive transplantation may be carried out with a non-human warm-blooded animal of the same class or order, as well as those of the same species or genus.

The human cells can be transplanted into any site of the animal as long as the human cell proliferates in that site: for example, in the allantoic cavity, or intravenously, intraperitoneally, or subcutaneously.

Alternatively, the human cells may be proliferated by placing them in a conventional diffusion chamber of any of various shapes and sizes, equipped with a suitable means which prevents contamination of the chamber with carrying the animal cells, but supplies the human cells with the nutrient body fluid of the animal, e.g., a membrane filter, ultrafilter or hollow fiber of a nominal pore size of about $10^{-7}$–$10^{-5}$ m; embedding, for example, intraperitoneally, the chamber in the animal; and allowing the human cells to proliferate in the chamber while receiving the nutrient body fluid from the animal.

Furthermore, the diffusion chamber can be designed and placed, e.g. on the animal, so that the nutrient fluid in the chamber can circulate freely through the chamber. The culture in the chamber can be observed during the cell proliferation through transparent side window(s), equipped on the chamber wall(s), and/or the chamber per se can be replaced at intervals with a fresh one, both to continue the cell proliferation over the period of the life span of the animal without sacrificing and to augment much more the cell production per animal. Since due to the absence of direct contact of the human cells with the animal cells, such a diffusion chamber technique elicits much less undesirable immunoreaction. Thus, any non-human warm-blooded animal may be readily used, without pretreatment to reduce such immunoreaction, and the proliferated viable human cells can be harvested easily from the diffusion chamber.

Feeding of the animal can be carried out in the usual way, and no special care is required even after the transplantation. The period required to obtain maximum cell proliferation is generally from one to 10 weeks. The number of the human cells so obtained is about $10^7$–$10^{12}$ cells per animal or more. More particularly, according to the present invention, the transplanted human cells increase by about $10^2$–$10^7$-fold or more, which is about $10$–$10^6$-fold or higher than that obtained by inoculating and proliferating the human cells on an in vitro nutrient culture medium. This is very favorable in the production of LK 2.

Any method is employable in the present invention as long as LK 2 production can be induced in the proliferated human cells therewith. The proliferated human cells may be exposed to an LK 2 inducer in the animal used as the host for cell proliferation: For example, human cells, proliferated in ascite in suspension, or tumor cells, formed, e.g., subcutaneously, may be directly exposed in vivo to an LK 2 inducer to induce LK 2 production, and the accumulated LK 2 harvested from the ascite, serum and/or tumor, followed by purification of the LK 2. Alternatively, the proliferated human cells may be harvested from the animal and then exposed in vitro to an LK 2 inducer. For example, the proliferated human cells, obtained by harvesting from ascite suspension, or extracting and disaggregating the tumor mass(es), formed, e.g., subcutaneously, may be suspended in a nutrient culture medium, prewarmed to a temperature of about 20°–40° C., to give a cell density of about $10^5$–$10^8$ cells/ml, and exposed in vitro to an LK 2 inducer, followed by recovering the accumulated LK 2 from the culture.

When a conventional-type diffusion chamber is used, exposure of the proliferated human cells to an LK 2 inducer is carried out in the chamber or after harvesting.

The human cells so obtained may be cultured in vitro for an additional 1–4 days to regulate their generation time, prior to the LK 2 induction.

The LK 2 production per animal may be further augmented by employing one or more of the following methods:

(1) a method wherein the proliferated human cells are exposed to an LK 2 inducer in the animal, which has been used as the host for the cell proliferation, and then harvested from certain site(s) of the animal or its whole body, followed by in vitro exposure of the human cells to an LK 2 inducer, (2) a method wherein the human cells are repeatedly exposed to an LK 2 inducer, and (3) a method wherein the diffusion chamber embedded in or connected to the animal is replaced at intervals with a fresh one.

The LK 2 inducers usable in the present invention are conventional α-interferon inducers (IFN-α inducers), such as virus, nucleic acid and nucleotide; and conventional γ-interferon inducers (IFN-γ inducers), such as, phytohaemagglutinin, concanavalin A, pokeweed mitogen, lipopolysaccharide, endotoxin, polysaccharide and bacteria. Antigens act on sensitized cells as an LK 2 inducer.

The LK 2 production can be augmented by a combined use of IFN-α and IFN-γ inducers as LK 2 inducer. It has been confirmed that such combination induces simultaneous production of human-specific interferon (HuIFN). This is very advantageous in a simultaneous and low-cost mass-production of two or more biologically-active substances, i.e., invaluable LK 2 and HuIFN, as well as in a much more effective utilization of human cells.

The LK 2 so obtained can be recovered by one or more purification and/or separation procedures, e.g., salting-out, dialysis, filtration, centrifugation, concentration, and/or lyophilization. If a much more purificated LK 2 preparation is desirable, a preparation of the highest purity can be obtained by the above described procedure(s) in combination with other conventional procedure(s), e.g., adsorption and desorption with ion exchange, gel filtration, isoelectric point fractionation, electrophoresis, ion exchange chromatography, high-performance liquid chromatography, column chromatography, and/or affinity chromatography.

Immobilized monoclonal antibodies obtained by binding a monoclonal anti-LK 2 antibody, which will be described hereinafter, onto a suitable water-insoluble carrier, e.g., BrCN-activated Sepharose, a product of Pharmacia Fine Chemical AB, Uppsala, Sweden, can be advantageously used to speed up and facilitate purification of LK 2.

It was confirmed that LK 2 thus obtained has the following physicochemical properties:

(1) Molecular weight:
20,000±2,000 daltons;

(2) Isoelectric point:
pI=6.2±0.3;

(3) Electrophoretic mobility:
on Disc-PAGE, Rf=0.29±0.02;

(4) uv-Absorption spectrum:
an absorption maximum at a wave length of about 280 nm;

(5) Solubility in solvents:
soluble in water, saline and phosphate buffer,
scarcely soluble or insoluble in ethyl ether, ethyl acetate or chloroform;

(6) Coloring reaction:
protein-positive by Lowry's method or the microburet method,
saccharide-positive by the phenol-sulfuric acid method or anthrone-sulfuric acid method;

(7) Biological activities:
cytotoxic on L 929 cells,
cytostatic on KB cell,
substantially free from interferon activity;

(8) Stability in aqueous solution:
stable up to 60° C. when incubated at pH 7.2 for 30 minutes,
stable in the pH range of 4.0–11.0 when incubated at 4° C. for 16 hours; and (9) Stability on cryopreservation:
stable at −10° C. over a period of one month or longer.

It has also been confirmed that LK 2 does not effect any substantial cytolysis on normal human cells, but effects a remarkable cytolysis on a variety of human tumor cells as well as on the mouse fibroblastoid line, L 929, to kill these cells. Thus, LK 2, e.g., in the form of a composition, is suitable use against prophylactic and/or therapeutic for LK 2-sensitive diseases, e.g., malignant tumors, and more particularly, against various malignant human tumors, the treatment of which has previously been deemed very difficult.

According to one aspect of the present invention, the antioncotic effects of conventional chemotherapeutics can be enhanced with an enhancer that contains LK 2 as the effective component.

The dose of chemotherapeutics can be reduced to about $\frac{1}{2}$–1/1000, of the conventional dose because the antioncotic effect to chemotherapeutics can be greatly enhanced with the enhancer of the present invention. In addition, the use of the enhancer broadens the tumor spectra of chemotherapeutics, and enables the treatment of drug-resistant tumors.

The chemotherapeutics usable in the invention include for example, one or more alkylating agents, such as melphalan, cyclophosphamide, ifosfamide, estramustine sodium phosphate, busulfan, imorposulfan tosilate, N-methyl-3,3'-dimesyloxydipropylamine biphenyl-4,4'-disulfonate, carboquone, thio-TEPA, carmustine, nimustine hydrochloride, streptozocin, dacarbazine, and pipobroman; metabolic antagonists, such as methotrexate, fluorouracil, tegaful, carmoful, cytarabine, ancitabine hydrochloride, enocitabine, 6-mercaptopurine, and thioinosine; antioncotic, antibiotics such as doxorubicin, daunorubicin, aclarubicin, bleomycin, peplomycin, mitomycin C, actinomycins D and C, chromomycin $A_3$, mithramycin, and neocarzinostatin; and plant alkaloids, such as vincristine sulfate, vinblastine sulfate, vindesine sulfate, and podophyllotoxin. In the case of treating prostate cancer or breast cancer, one or more antioncotic hormones, such as predonisolone, methyltestosterone and conjugated estrogen, can be desirably used in combination.

Conditions for combining these chemotherapeutics and LK 2 should be desirably chosen, and not restricted.

The process for producing a monoclonal antibody according to the present invention comprises immunizing a non-human warm-blooded animal using LK 2 as the antigen; isolating the antibody-producing cells from the body of the animal; fusing the antibody-producing cells with myeloma cells; selecting from the resultant hybrid cells a clone capable of producing an antibody which is specific to LK 2; proliferating the clone; and allowing the proliferated cell to produce the monoclonal antibody specific to LK 2.

Such immunization can be obtained by injecting, e.g., intravenously, intraperitoneally or subcutaneously, an aqueous solution, emulsion or suspension of LK 2 as the antigen into a suitable non-human warm-blooded animal, e.g., chicken, pigeon, dog, cat, monkey, goat, pig, cow, horse, rabbit, guinea pig, rat, hamster or mouse; and feeding the animal for three days or longer to induce antibody production. A conjugate of LK 2 and a saccharide obtainable according to the teaching of Japan Patent Publication No. 23,847/83 is also employable as the antigen.

The antigen may be injected in single dosage or, if necessary, in two or more dosages at interval(s) of about 3-30 days.

The spleen cells of the immunized animal in which antibody production has been induced are fused with myeloma cells of the same or a different species with a suitable procedure, e.g., those reported by Kohler, G. et al. in *Nature*, Vol. 256, pp. 495-497 (1975), and *European Journal of Immunology*, Vol. 6, pp. 511-519 (1976). The hybrid cells so obtained are then selected and cloned, after which the clone(s) is cultured in vitro or in vivo, followed by recovery of the accumulated highly-specific monoclonal antibody from the resultant culture. Specifically, an in vivo procedure is more preferable than the in vitro procedure because the former procedure attains a much higher proliferation of the clone and a much higher production of the monoclonal antibody without using expensive serum.

In the in vivo procedure, the clone is proliferated while utilizing the nutrient body fluid of a non-human warm-blooded animal of the same or a different species than that used in the immunization by transplanting the clone to such a non-human warm-blooded animal, or inoculating the clone in a conventional-type diffusion chamber devised to receive the nutrient body fluid of such an animal, and the accumulated monoclonal antibody is recovered from the body fluids, such as ascite and serum. Alternatively, after proliferating in vivo, the clone may be cultured on a serum-free culture medium for an additional 1-5 days, followed by recovery of the accumulated monoclonal antibody from the resultant culture.

The monoclonal antibody so obtained can be recovered easily with one or more separation and/or purification procedures, e.g., salting-out, dialysis, filtration, centrifugation, concentration and/or lyophilization. If a much higher purification is desirable, a preparation of the highest purity can be obtained by the above-mentioned procedure(s) in combination with other conventional procedure(s), e.g., adsorption and desorption with ion exchange, gel filtration, isoelectric point fractionation, electrophoresis, ion exchange chromatography, high-performance liquid chromatography, column chromatography, and/or affinity chromatography. The recovery yield of the monoclonal antibody can be improved advantageously by use of an immobilized LK 2 gel obtained by binding a high-purity LK 2 onto a suitable water-insoluble carrier, e.g., BrCN-activated Sepharose.

The monoclonal antibody obtained according to the present invention is favorably usable as a ligand for affinity chromatography directed to LK 2 production, as well as in diagnosis of a variety of human diseases because of its specificity to LK 2 which damages malignant tumors.

LK 2 titers are assayed by use of either KB cell or L 929 cell as the target cell: When KB cell is used, the cytostatic activity on KB cell is determined according to the method described in *Cancer Chemotherapy Reports Part* 3, Vol. 3, No. 2, September (1972); When L 929 cell is used, the cytotoxic activity on L 929 cell in the presence of actinomycin D was determined by the method described in *Lymphokines*, Vol. 2, pp. 245-249, "Tumor Necrosis Factor", edited by Pick, E., published by Academic Press Inc. (1981). One unit is defined as the amount of LK 2 that kills 50% of L929 cells when cultured in the presence of actinomycin D for 18 hours. Throughout the present specification, the latter method using L 929 cell was employed unless otherwise specified.

The titers of HuIFN were assayed by the conventional plaque-reduction method using FL cells of human amnion origin described in *Protein, Nucleic Acid and Enzyme*, Vol. 20, No. 6, pp. 616-643 (1975).

The haemagglutination titers were assayed according to the method reported by Salk, S. E., *The Journal of Immunology*, Vol. 49, pp. 87-98 (1944).

The following Experiments further detail the present invention.

EXPERIMENT A-1

Preparation of Partially-Purified LK 2

Newborn hamsters were injected with about 4 mg/hamster of conventional antiserum prepared from rabbit to weaken their possible immunoreaction upon heterotransplantation, transplanted subcutaneously with about $1 \times 10^7$ cells/hamster of BALL-1 cell, a human lymphoblastoid line, and fed in usual way for three weeks. The tumor masses, formed subcutaneously, were extracted, minced, and disaggregated in saline. The cell suspension so obtained was then washed with RPMI 1640 medium (pH 7.2) supplemented with serum, and resuspended in a fresh preparation of the same culture medium to give a cell density of about $2 \times 10^6$ cells/ml. To the cell suspension was added Sendai virus (about 400 haemagglutination titer/ml), and the culture was incubated at 37° C. for 24 hours to induce LK 2 production.

The culture was centrifuged at about $1,000 \times g$ and about 4° C., and the resultant precipitate was removed. The supernatant so obtained was dialyzed against saline containing 0.01M phosphate buffer (pH 7.2) for 20 hours, and treated with a membrane filter. The filtrate was then passed through a column of "NK-2", an immobilized monoclonal anti-HuIFN-alpha antibody commercialized by CELLTECH, Burkshire, UK, and the unadsorbed fraction was collected. An active fraction was recovered from this fraction by means of chromatofocusing, concentrated, and lyophilized to obtain a pulverulent product with LK 2 activity.

The specific activity of the product was about $10^6$ units/mg protein. The LK 2 yield was about $2.0 \times 10^7$ units per hamster.

EXPERIMENT A-2

Preparation of Anti-LK 2 Antibody

An LK 2 preparation, obtained by the method in Experiment A-1, was dissolved in saline to give a concentration of about 0.05 w/v % as protein, and to the solution was added the same volume of Freund's complete adjuvant. Mice were immunized by subcutaneously injecting 0.2 ml aliquots of the mixture so obtained, and boosting seven days after the first injection. After inducing anti-LK 2 antibody production in the antibody-producing cells of the animals, the spleens of the animals were extracted, minced, disaggregated, and suspended together with a mouse myeloma cell line, $P_3$-X63-Ag8, purchased from Flow Laboratories Inc., Rockville, Md, U.S.A., in serum-free Eagle's minimal essential medium (pH 7.2) containing 50 w/v % polyethylene glycol 1000, prewarmed to 37° C., to give a respective cell density of $10^4$ cells/ml, followed by a 5-minute standing of the resultant mixture. Thereafter, the mixture was diluted 20-times in a fresh preparation of the same culture medium, and the hybridoma cells capable of growing on the hypoxanthine, aminopterin, thymidine containing medium were collected according to the method reported by Davidson, R. L. and Gerald, P. S. in *Somatic Cell Genetics*, Vol. 2, No. 2, pp. 175-176 (1976) to clone the hybridoma cells capable of producing anti-LK 2 antibody. Mice were transplanted intraperitoneally with the cloned hybrodoma cells in a dosage of about $10^6$ cells per mouse, fed for two weeks, and sacrificed. The body fluids of the animals, such as ascite fluid and blood, were recovered, centrifuged, and salted out with ammonium sulfate, followed by collection of the fractions sedimented at 30-50% saturation. These fractions were dialyzed, and subjected to affinity-chromatography using an immobilized anti-(LK 2 antibody) gel obtained by reacting an LK 2 specimen, prepared by the method in Experiment A-1, with BrCN-activated Sepharose at ambient temperature, to obtain an anti-(LK 2 antibody) fraction which was then dialyzed, concentrated and lyophilized.

The resultant pulverulent product exhibited an immunologically-specific neutralization to the cytotoxic activity of LK 2.

The stability of the monoclonal antibody in aqueous solution was studied by assaying the residual neutralizing activities after incubating under prescribed condition: On incubation at pH 7.2 and different temperatures for 30 minutes, 80% or more of the activity was retained at 60° C., but 90% or more was lost at 70° C. After incubation at 4° C. and different pH levels for 16 hours, the activity was stable in the pH range of 4.0-11.0, but was lost by 90% or more at pH 2.0.

On studying the properties of the monoclonal antibody, the monoclonal antibody was found not to be resistant to 2-mercaptoethanol, and effected a specific antigen-antibody reaction with anti-mouse immunoglobulin M antibody. Thus, the present monoclonal antibody is grouped into the class of immunoglobulin M antibody.

EXPERIMENT A-3

Preparation and Physicochemical Properties of Highly-Purified LK 2

A partially-purified LK 2 specimen, obtained by the method in Experiment A-1, was subjected to affinity-chromatography using an immobilized gel of the monoclonal antibody prepared by the method in Experiment A-2, to collect LK 2 fractions which were then dialyzed, concentrated and lyophilized.

The resultant was a highly-purified LK 2 preparation with a specific activity of about $10^9$ units/mg protein.

The physicochemical properties of LK 2 were studied with this preparation.

(1) Molecular weight:
The molecular weight of LK 2 was determined by the electrophoretic methods using SDS-polyacrylamide gel described in Weber, K. and Osborn, M., *Journal of Biological Chemistry*, Vol. 244, page 4,406 (1969). Columns of 10% acrylamide gel were loaded with about 10 μg aliquots of the preparation in the presence of 0.1% SDS, and charged with 8 mA per column for four hours to effect electrophoresis. After extraction and subsequent LK 2 assay of the active fractions, the molecular weight of LK 2 was found to be 20,000±2,000 daltons.

(2) Isoelectric point:
A 2 hours, 25 W electrofocusing of the preparation using "AMPHOLINE PAGPLATE (pH 3.5-9.5)", a gel product for electrofocusing, commercialized by LKB-Produkter AB, Stockholm, Sweden, gave an isoelectric point pI of 6.2±0.3.

(3) Electrophoretic mobility:
According to the method described in Davis, B. J., *Annals of New York Academy of Sciences*, Vol. 121, page 404 (1964), about 10 μg aliquots of the preparation were loaded on columns of 7.5% acrylamide gel, subjected to electrophoresis at pH 8.3 and 3 mA per column for two hours, extracted, and assayed for LK 2 activity to obtain an electrophoretic mobility Rf of 0.29±0.02.

(4) uv-Absorption spectrum:
After analyzing the uv-spectrum of the preparation with UV-250 spectrometer, a product of Shimadzu Seisakusho KK, Kyoto, Japan, an absorption maximum was found at a wave length of about 280 nm.

(5) Solubility in solvent:
Soluble in water, saline and phosphate buffer solution; scarcely soluble or insoluble in ethyl ether, ethyl acetate and chloroform.

(6) Coloring reaction:
Protein-positive by Lowry's method and the microburet method; saccharide-positive by the phenol-sulfuric acid method and the anthrone-sulfuric acid method.

(7) Biological activity:
A cytotoxic activity on L929 cell and no substantial growth-inhibitory activity on KB cell were noted.
No substantial HuIFN activity was noted.

(8) Stability in an aqueous solution:
(i) Heat stability:
About $1 \times 10^5$ units/ml aliquots of the preparation were incubated at pH 7.2 and different temperatures for 30 minutes, and the residual cytotoxic activities were assayed. As a result, LK 2 was found stable up to 60° C.

(ii) pH Stability:
0.1 ml aliquots of the preparation ($1 \times 10^6$ units/ml) were combined with 1 ml buffer solution of different pH levels, i.e. McIlvaine buffer at pH 2-7; phosphate buffer, pH 7-8; glycine-NaOH buffer, pH 8-11, and incubated at 4° C. for 16 hours. Thereafter, 0.1 ml of the incubated mixture was adjusted to pH 7.2 with 0.05M phosphate buffer (pH 7.2), and the residual activity was assayed. As a result, LK 2 was found stable in the pH range of 4.0-11.0.

(iii) Stability to "DISPASE":
To about $1 \times 10^5$ units/per ml of the preparation was added "DISPASE", a protease enzyme of Bacillus microorganism, commercialized by Godo Shusei Co., Ltd., Tokyo, Japan, to give an enzyme activity of 100 units/ml, and the mixture was incubated at pH 7.2 and 37° C. for two hours. During the incubation, small portions of the mixture were sampled periodically, and combined with calf serum albumin to give a concentration of 1 w/v % to suspend the enzymatic reaction. On assaying the LK 2 activities in the samples, LK 2 was susceptive to DISPASE treatment and lost its activity as the enzymatic reaction proceeded.

(9) Stability to cryopreservation:
The LK 2 preparation was stored in aqueous solution at −10° C. and pH 7.2 for one month, thawed and assayed. No decrease in activity was noted.

From these evidences, it is clear that LK 2 has physicochemical properties distinguishable from those of known lymphokines such as LT, TNF or IFN. Also, the present monoclonal antibody is novel because it exhibits an immunologically-specific neutralization with the cytotoxic activity of the novel lymphokine LK 2.

EXPERIMENT B-1

Cytostatic Effect on Malignant Tumor Cells

The cytostatic activity of LK 2 on several human cells was studied with LK 2 preparations obtained by the method in Experiments A-1 and A-3.

One human cell suspension ($10^6$ cells) listed in Table I was suspended in 1 ml of conventional nutrient medium supplemented with foetal calf serum, cultured for one day, added with 0.1 ml of a saline containing either 50 units or 500 units of an LK 2 preparation, prepared by the method in Experiment A-1 or A-3, and incubated at 37° C. for two days. After completion of the culture, the viable cells were stained with neutral red, a type of staining agent, according to the method described in *Applied Microbiology*, Vol. 22, No. 4, pp. 671–677 (1971), and the staining agent was eluted by use of an acidified ethanol solution. The number of the viable cells was determined by measuring the absorbance of the eluate at a wave length of 540 nm.

TABLE I

| Name of cell line | Source of cell line | LK 2 at Experiment A-1 | | LK 2 at Experiment A-3 | |
|---|---|---|---|---|---|
| | | 50 units | 500 units | 50 units | 500 units |
| HEp#2* | Larynx epidermoid carcinoma | 33 | 40 | 46 | 68 |
| PC-8* | Lung carcinoma | 26 | 37 | 56 | 80 |
| MKN 7* | Gastric cancer | 35 | 41 | 60 | 77 |
| HLE* | Liver carcinoma | 32 | 38 | 55 | 71 |
| HeLa* | Cervix epitheloid carcinoma | 24 | 35 | 46 | 68 |
| L-132** | Embryonic lung | 3 | −2 | 1 | −3 |
| Chang liver** | Liver | 2 | −3 | −4 | −1 |
| Giradi heart** | Heart | −2 | 2 | −1 | −2 |

Note:
*indicates human cell lines of malignant tumor origins;
**those of normal origins.

As a control, 0.1 ml of an LK 2 free saline was used.

Growth inhibition (%) was calculated with the following equation:

$$\text{Growth inhibition (\%)} = \left(1 - \frac{\text{Absorbance when } LK\ 2 \text{ used}}{\text{Absorbance of the control}}\right) \times 100$$

The results are given in Table I.

These results confirm that LK 2 does not substantially affect normal cells, but greatly inhibits the growth of various malignant tumor cells. It was also that the effect of a partially-purified LK 2 compares well with that of highly-purified one.

EXPERIMENT B-2

A group of ten BALB/c mice was transplanted with Mrth A cell of mouse sarcoma origin. From the tenth day after the transplantation, the mice were injected intravenously with saline containing an LK 2 preparation, obtained by the method in Experiment A-3, in a dosage of 100 or 1,000 units/kg daily for 15 days. Thereafter, the mice were sacrificed, and the tumor masses, formed in the animals, were measured.

The results are shown in Table II.

TABLE II

| Treatment | Dosage per day (units/kg) | Tumor mass (g) |
|---|---|---|
| Control | 0 | 5.7 ± 0.7 |
| LK 2 | 100 | 3.3 ± 0.4* |
| | 1,000 | 2.8 ± 0.4* |

Note:
*means the values are statistically significant against the control in a level of significance of 5%.

EXPERIMENT B-3

A group of BALB/c nude mice was transplanted subcutaneously in their dorsum areas with small fragments of human breast cancer tissue.

After the tumor masses grew to about 200 mm³ in the bodies of the animals, saline containing an LK 2 preparation, obtained by the method in Experiment A-1 or A-3, was injected intravenously once every day in a dosage of either 100 units/kg or 1,000 units/kg for twenty days. Thereafter, the animals were sacrificed, and the resultant tumor masses were weighed.

The results are given in Table III.

TABLE III

| Treatment | Dosage per day (units/kg) | Tumor mass (g) |
|---|---|---|
| Control | 0 | 10.8 ± 1.0 |
| LK 2 | 100 | 7.3 ± 0.7* |
| at Experiment A-1 | 1,000 | 6.8 ± 0.5* |
| LK 2 | 100 | 6.4 ± 0.5* |
| at Experiment A-3 | 1,000 | 5.6 ± 0.7* |

Note:
*means the values were statistically significant against the control in a level of significance of 5%.

EXPERIMENT B-4

A group of BALB/c nude mice was transplanted subcutaneously in their dorsum areas with small fragments of human breast cancer tissue similarly as in Experiment B-3.

After the tumor masses grew to about 200 mm³ in the bodies of the animals, saline containing an LK 2 preparation, obtained by the method in Experiment A-3, and/or an HuIFN-α preparation, was injected intravenously once every day for twenty days. Thereafter, the animals were sacrificed, and the resultant tumor masses were weighed.

As the control, an LK 2- and HuIFN-α-free saline was used.

The results are given in Table IV.

These evidences clearly show that the combined use of LK 2 and HuIFN-α extremely enhances the antioncotic effect of HuIFN-α.

TABLE IV

| Treatment | Dosage per day (units/kg) | Tumor mass (g) |
|---|---|---|
| Control | 0 | 10.8 ± 1.0 |
| LK 2 | 100 | 6.4 ± 0.5* |
| HuIFN-α | 1,000 | 6.7 ± 0.5* |
| LK 2 plus HuIFN-α | 100 1,000 | 5.3 ± 0.4* |

Note:
*means the values were statistically significant against the control in a level of significance of 5%.

EXPERIMENT B-5

An acute toxicity test, wherein a group of 20-day old mice was administrated with an LK 2 preparation, obtained by the method in Experiment A-3, confirmed that the toxicity of the preparation was extremely low, i.e., an $LD_{50}$ $10^9$ units or more, upon intraperitoneal injection.

As is obvious from the above experiments, LK 2 exhibits a strong cytostatic effect on malignant tumors in vitro as well as in vivo. Furthermore, the administration of LK 2 is very safe as a high dosage does not practically affect normal cells, while a low dosage remarkably affects tumor cells.

The effective dosage of LK 2 generally falls in the range of 5-500,000,000 units/day for an adult: more particularly, for local administration, e.g., in the form of local injection or collyrium, 5-10,000,000 units/day; for percutaneous or permucosal administration, e.g., in the form of ointment or suppository, 10-50,000,000 units/day; for systemic administration, e.g., intravenous- or intramuscular injection, 50-100,000,000 units/day; and oral administration, 500-500,000,000 units/day, but the dosage is freely variable dependent upon the instructions and the patient's symptoms.

Although LK 2 can be prepared into a medicine in the usual way after admixing with a suitable conventional carrier, base and/or vehicle, the LK 2 content thereof should be at least 5 units/g in view of its toxicity, effective dosage, and safety.

The shape and form of prophylactic- and/or therapeutic agents for LK 2-sensitive diseases can be freely chosen: for example, for oral administration, it may be formulated into preparations for enteric uses, e.g., capsule, tablet or powder; for rectal administration, suppository; for injection, it may be, for example, prepared into a lyophilized injection which is dissolved, prior to use, into an injection solution with distilled water, as well as in the forms of collunarium, collyrium or ointment.

As an example of the treatment of a malignant tumor patient, a tumor tissue fragment extracted from the patient may be treated in vitro with LK 2 to enhance the immunogenicity of the tissue fragment, and that treated tissue fragment administered to the patient to obtain a much more effective treatment of the malignant tumor.

Combined uses of LK 2 with antioncotic(s), for example, lymphokines, such as HuIFN, TNF, LT and T-cell growth factor (TCGF); antioncotic polysaccharides, such as β-1,3-glucan, arabinomannan, lipopolysaccharide, OK-432 (picibanil), PSK (krestin) and lentinan; metabolic antagonists such as methotrexate and fluorouracil; and antioncotic antibiotics, such as doxorubicin and mitomycin C are very advantageous because such combined uses extremely enhance the antioncotic effect of LK 2.

Specifically, it has been elucidated that LK 2 enhances the antioncotic effect of chemotherapeutics.

The antioncotic effect-enhancing property of LK 2 will be explained hereinafter.

EXPERIMENT C-1

Enhancement of Antioncotic Effect of Chemotherapeutics by LK 2

The enhancement of antioncotic effect of chemotherapeutics by LK 2 was studied with malignant tumor cells.

One human malignant tumor cell suspension ($10^6$ cells) was inoculated on 1 ml of conventional-type nutrient culture medium supplemented with foetal calf serum, and then cultured for one day. Thereafter, there was added to the culture 0.1 ml of saline containing 100 units of an LK 2 specimen, prepared by the method in Experiment A-3, and/or a chemotherapeutic, and cultured for an additional two days at 37° C.

TABLE V

| Cell line | None + | ACNU − | ACNU + | 5-FU − | 5-FU + | ADM − | ADM + | MMC − | MMC + | VCR − | VCR + |
|---|---|---|---|---|---|---|---|---|---|---|---|
| HEp#2 (Larynx epidermoid carcinoma) | 52 | 4 | 67 | 8 | 80 | 13 | 70 | 10 | 72 | 5 | 66 |
| PC-8 (Lung carcinoma) | 62 | 2 | 71 | 10 | 85 | 6 | 71 | 5 | 68 | 8 | 72 |
| MKN 7 (Gastric cancer) | 62 | 4 | 73 | 6 | 77 | 5 | 69 | 3 | 73 | 6 | 70 |
| HLE (Liver carcinoma) | 57 | 5 | 75 | 8 | 81 | 7 | 73 | 12 | 74 | 10 | 69 |
| HeLa (Cervix epitheloid carcinoma) | 51 | 5 | 71 | 12 | 69 | 7 | 62 | 7 | 61 | 10 | 63 |

Note:
+, with LK 2; −, without LK 2; and growth inhibition (%) to tumor cell.

As the control, an LK 2- and chemotherapeutic-free saline was used.

After completion of the culture, the number of viable cells was counted in accordance with the method in Experiment B-1, and the growth inhibition (%) was then determined.

The concentrations of the tested chemotherapeutics were as follows: nimustine hydrochloride (ACNU), $1.0 \times 10^{-6}$ g/ml culture; fluorouracil (5-FU), $1.5 \times 10^{-8}$ g/ml culture; doxorubicin (ADM), $1.0 \times 10^{-10}$ g/ml culture; mitomycin C (MMC), $2.5 \times 10^{-9}$ g/ml culture; and vincristine sulfate (VCR), $1.5 \times 10^{-10}$ g/culture.

The results are given in Table V.

This evidence clearly shows that LK 2 enhances extremely the antioncotic effect of chemotherapeutics.

EXPERIMENT C-2

A group of BALB/c nude mice was transplanted subcutaneously in their dorsum areas with small fragments of human breast cancer tissue.

After the tumor masses grew to about 200 mm$^3$ in the bodies of the animals, saline containing an LK 2 preparation, obtained by the method described in Experiment A-3, and/or mitomycin C (MMC) was injected intravenously once every day for twenty days.

Thereafter, the animals were sacrificed, and the resultant tumor masses were weighed.

As the control, an LK 2- and chemotherapeutic-free saline was used.

The results are given in Table VI.

TABLE VI

| Treatment | Dosage per day | Tumor mass (g) |
|---|---|---|
| Control | 0 | 10.8 ± 1.0 |
| LK 2 | 100 units/kg | 6.4 ± 0.5* |
| MMC | 1 mg/kg | 5.1 ± 0.4* |
| LK 2 plus MMC | 100 units/kg 0.1 mg/kg | 4.8 ± 0.4* |

Note:
*means the values were statistically significant against the control in a level of significance of 5%.

This evidence clearly shows that LK 2 enhances extremely the antioncotic effect of chemotherapeutics even in vivo.

The aforementioned evidence confirms that a combination of a chemotherapeutic with LK 2 shows a high antioncotic effect as compared to the use of the chemotherapeutic alone at a low concentration to give an insufficient antioncotic effect.

The use of LK 2 as the enhancer for chemotherapeutics extremely reduces the practical chemotherapeutic concentration, prevents the elicitation of side-effects, and widens extremely the tumor spectra of the chemotherapeutics.

The enhancer containing LK 2 according to the present invention exhibits the antioncotic effect-enhancing activity when used together with chemotherapeutics.

The enhancer is premixed with a chemotherapeutic, and the resultant product is administered simultaneously in a single route. Alternatively, either the enhancer or a chemotherapeutic is first administered, then the remainder is administered in the same or different route.

The following Examples A, B and C illustrate LK 2 production, pharmaceutical compositions containing LK 2, and the LK 2-specific monoclonal antibody, respectively.

EXAMPLE A-1

BALL-1, a human lymphoblastoid line, was inoculated on Eagle's minimal essential medium (pH 7.4), supplemented with 20% foetal calf serum, and cultured in vitro in suspension at 37° C. in the usual way. The proliferated human cells were then washed with serum-free Eagle's minimal essential medium (pH 7.4), and resuspended in a fresh preparation of the same culture medium to give a cell density of about $1 \times 10^7$ cells/ml. To the cell suspension was added Sendai virus in a dosage of about 1,000 haemagglutination titers/ml, and the culture was incubated at 38° C. for one day to induce LK 2 production. After centrifuging the resultant culture at about $1000 \times g$ and about 4° C., the supernatant was dialyzed against saline containing 0.01M phosphate buffer (pH 7.2) for 15 hours, and treated with a membrane filter. The filtrate was then passed through a column of anti-HuIFN antibody similarly as in Experiment A-1, and the unadsorbed fraction was purified similarly as in Experiment A-3 by means of affinity chromatography using a column of an anti-LK 2 antibody-bound gel, and concentrated to obtain a concentrate with a specific LK 2 activity of about $10^9$ units/mg protein.

The yield was about $1.5 \times 10^6$ units/liter of the induced cell suspension.

EXAMPLE A-2

Newborn hamsters were injected with about 4 mg/hamster of conventional antiserum prepared from rabbit to weaken their possible immunoreaction upon herero-transplantation, transplanted subcutaneously with about $1 \times 10^7$ cells/hamster of BALL-1 cell, a human lymphoblastoid line, and fed in usual way for three weeks. The tumor masses, about 15 g each, formed subcutaneously in the animals, were extracted, minced, and disaggregated in saline. After washing with serum-free RPMI 1640 medium (pH 7.2), the proliferated cells were resuspended in a fresh preparation of the same culture medium to give a cell density of about $5 \times 10^6$ cells/ml. To the cell suspension was added Sendai virus and $E.\ coli$ endotoxin in respective dosages of about 1,000 haemagglutination titers/ml and about 10 μg/ml, and the culture was incubated at 37° C. for one day to induce LK 2 production. After centrifuging the culture at about $1,000 \times g$ and 4° C. to remove the sediment, the supernatant was dialyzed against saline containing 0.01M phosphate buffer (pH 7.2) for 21 hours, and treated with a membrane filter. The filtrate was purified with a column of antibody similarly as in Example A-1, and the eluate solution was concentrated and lyophilized to obtain a pulverulent product with a specific LK 2 activity of about $10^9$ units/mg protein.

The yield was about $3.2 \times 10^7$ units.

EXAMPLE A-3

Adult nude mice were transplanted intraperitoneally with TALL-1, a human lymphoblastoid line, fed in usual way for five weeks, injected intraperitoneally with Newcastle disease virus (about 3,000 haemagglutination titers per nude mouse) which had been substantially preinactivated with uv-irradiation, and sacrificed 24 hours after the injection, followed by harvest of their ascite fluids. The ascite fluids were purified, concentrated, and lyophilized similarly as in Example A-2 to obtain a pulverulent product with LK 2 activity.

The yield was about $3.5 \times 10^6$ units per nude mouse.

EXAMPLE A-4

Adult mice were irradiated with about 400 rem of x-ray to weaken their immunoreaction, transplanted subcutaneously with Mono-1, a human lymphoblastoid line, and fed in the usual manner for three weeks. The tumor masses, about 10 g each, formed subcutaneously in the animals, were extracted and disaggregated similarly as in Example A-2. The human cells thus obtained were suspended similarly as in Example A-2, after which Sendai virus and concanavalin A were added to the resultant cell suspension in respective dosages of about 500 haemagglutination titers/ml and 0.8 μg/ml, and the culture was incubated at 37° C. for one day to induce LK 2 production. Thereafter, the culture was purified, concentrated, and lyophilized similarly as in Example A-2 to obtain a pulverulent product with LK 2 activity.

The yield was about $2.0 \times 10^7$ units per mouse.

EXAMPLE A-5

Newborn hamsters were transplanted with Namalwa (ATCC CRL 1432), a human lymphoblastoid line, similarly as in Example A-2, and fed in the usual way for four weeks. The tumor masses, about 20 g each, formed subcutaneously in the animals, were extracted and disaggregated to obtain a cell suspension having a cell density of about $3 \times 10^6$ cells/ml. To the cell suspension was added Sendai virus in a dosage of about 1,000 haemagglutination titers/ml, and the culture was incubated at 36° C. for two days to induce LK 2 production. The culture was purified and concentrated similarly as in Example A-1 to obtain a concentrate with LK 2 activity.

The yield was about $2.2 \times 10^7$ units per hamster.

EXAMPLE A-6

NALL-1, a human lymphoblastoid line, was suspened in saline, and placed in an about 10 ml cylindrical plastic diffusion chamber equipped with a membrane filter having a nominal pore size of about 0.5 $\mu$. The chamber was embedded intraperitoneally in an adult rat, and the animal was fed in the usual way for four weeks. After removal of the chamber, it was found that the cell density in the chamber was about $5 \times 10^8$ cells/ml, which was at least about $10^2$-fold higher in comparison with the case of proliferating in vitro in a $CO_2$ incubator using a nutrient culture medium. The human cells were suspended in culture medium similarly as in Example A-2, Newcastle disease virus (about 500 haemagglutination titers/ml), which had been preinactivated with uv-irradiation, and phytohaemagglutinin (about 50 $\mu$g/ml), were added and the culture was incubated at 37° C. for one day to induce LK 2 production. Thereafter, the culture was purified, concentrated, and lyophilized similarly as in Example A-2 to obtain a pulverulent product with LK 2 activity.

The yield was about $8 \times 10^6$ units per rat.

EXAMPLE A-7

CCRF-CEM (ATCC CCL 119), a human lymphoblastoid line, was inoculated in the allantoic cavities of embryonated eggs which had been incubated at 37° C. for five days, and the eggs were further incubated at this temperature for an additional one week. The proliferated human cells were harvested from the eggs, and suspended similarly as in Example A-1 to give a cell density of $5 \times 10^6$ cells/ml. To the cell suspension was then added Sendai virus (about 500 haemagglutination titers/ml), and the culture was incubated at 37° C. for one day to induce LK 2 production. The resultant culture was purified and concentrated similarly as in Example A-2 to obtain a pulverulent product with LK 2 activity.

The yield was about $7.0 \times 10^5$ units per ten embryonated eggs.

EXAMPLE B-1

Injection

Five hundred thousand units of an LK 2 specimen, prepared by the method in Example A-2, were dissolved in 200 ml saline, and filtered under sterile conditions by use of a membrane filter. Two ml aliquots of the filtrate were distributed into sterilized glass vials, lyophilized, and sealed to obtain a pulverulent injection.

The injection is favorably usable alone or as an enhancer in combination with a chemotherapeutic such as melphalan, methotrexate or doxorubicin for treating breast cancer, lung carcinoma, liver carcinoma and leukaemia.

EXAMPLE B-2

Injection

A pulverulent injection was prepared similarly as in Example B-1, except that $3 \times 10^8$ units of HuIFN-$\alpha$ derived from a human lymphoblastoid cell were dissolved in 200 ml of saline together with $5 \times 10^5$ units of LK 2.

The injection is favorably usable alone or as an enhancer in combination with a chemotherapeutic such as tegafur, mitomycin C or vincristine sulfate for treating breast cancer, lung carcinoma, liver carcinoma, and leukaemia, and its therapeutic efficacy is superior to that of the injection at Example B-1.

EXAMPLE B-3

Ointment

An LK 2 specimen, prepared by the method in Example A-3, was kneaded with a minimal amount of liquid paraffin to homogeneity. To the mixture was then added white petrolatum in the usual way to obtain an ointment with an LK 2 content of 20,000 units/g.

The ointment is favorably usable alone or as an enhancer in combination with a chemotherapeutic such as cyclophosphamide, fluorouracil or vincristine sulfate for treating skin carcinoma, breast cancer and lymphoma.

EXAMPLE B-4

Collyrium

A mixture of 800 ml distilled water, 5 ml $\beta$-phenylethyl alcohol and 20,000,000 units of an LK 2 specimen, prepared by the method in Example A-4, was admixed with sodium chloride in an additional amount of distilled water to obtain 1,000 ml of an isotonic solution.

The solution is favorably usable alone or as an enhancer in combination with a chemotherapeutic such as cytarabine or vincristine sulfate for treating retinoblastoma.

EXAMPLE B-5

Enteric Coated Tablet

Enteric coated tablets were prepared according to the conventional method by tabletting a mixture of starch, maltose, and an LK 2 specimen prepared by the method in Example A-7 to give an LK 2 content of 200,000 units per tablet (100 mg), followed by coating the tablets with phthalate ester of methyl cellulose.

The tablets are favorably usable alone or as an enhancer in combination with a chemotherapeutic such as doxorubicin, fluorouracil or mitomycin C for treating colon carcinoma and liver carcinoma.

EXAMPLE C-1

Mice were immunized similarly as in Experiment A-2, except that a high-purity LK 2 obtained by the method described in Experiment A-3 was used as the antigen. Thereafter, the spleen cells of the animals were suspended together with a mouse myeloma line, P3-NS-1/1-Ag4-1, a product of Dainippon Pharmaceutical Co., Ltd., Osaka, Japan, in a salt solution containing 140 mM NaCl, 54 mM KCl, 1 mM NaH$_2$PO$_4$, and 2 mM CaCl$_2$ to give a respective cell density of 10$^4$ cells/ml. To the cell suspension was added a fresh salt solution of the same composition but containing, in addition, Sendai virus, which had been inactivated with uv-irradiation, under ice-chilled conditions, and the mixture was allowed to stand for five minutes. Thereafter, the mixture was diluted about 20-times in 37° C. RPMI 1640 medium, and the hybridoma cells capable of producing anti-LK 2 antibody were cloned similarly as in Experiment A-2. The cloned hybridoma cells were transplanted intraperitoneally into 7-day old hamsters (about 10$^7$ cells per hamster) whose immunoreaction had been weakened with a conventional procedure, and the monoclonal antibody was recovered from the bodies of the animals similarly as in Experiment A-2.

Like the monoclonal antibody prepared in Experiment A-2, the product exhibited an immunologically-specific neutralization with the cytotoxic activity of LK 2.

The stability of the monoclonal antibody in aqueous solution was studied by assaying the residual neutralizing activities after incubating under prescribed conditions: On incubation at pH 7.2 and different temperatures for 30 minutes, 80% or more of the activity was retained at 60° C., but 90% or more was lost at 70° C. After incubation at 4° C. and different pH levels for 16 hours, the activity was stable in the pH range of 2.0–11.0.

On studying several properties of the monoclonal antibody, it was found that the present monoclonal antibody was resistant to 2-mercaptoethanol, and effects a specific antigen-antibody reaction with anti-mouse immunoglobulin G antibody. Thus, the present monoclonal antibody is grouped into the class of immunoglobulin G antibody.

EXAMPLE C-2

A monoclonal anti-LK 2 antibody was prepared similarly as in Example C-1, except that a mouse myeloma line, SP2/0-Ag14, available from Dainippon Pharmaceutical Co., Ltd., Osaka, Japan, was replaced for P3-NS-1/1-Ag4-1.

On studying the immunologically-specific neutralization by the monoclonal antibody with the cytotoxic activity of LK 2, a result similar to that obtained in Example C-1, was obtained. Thus, the monoclonal antibody is also grouped into the class of immunoglobulin G antibody.

While the invention has been particularly shown and described with reference to preferred embodiments thereof, it will be understood by those skilled in the art that the foregoing and other changes can be made therein without departing from the spirit and scope of the invention.

We claim:

1. A lymphokine (LK 2), which has the following physicochemical properties:
   (1) Molecular weight:
      20,000±2,000 daltons;
   (2) Isoelectric point:
      pI=6.2±0.3;
   (3) Electrophoretic mobility:
      on Disc-PAGE, Rf=0.29±0.02;
   (4) uv-Absorption spectrum:
      an absorption maximum at a wave length of about 280 nm;
   (5) Solubility in solvents:
      soluble in water, saline and phosphate buffer, scarcely soluble or insoluble in ethyl ether, ethyl acetate or chloroform;
   (6) Coloring reaction:
      protein-positive by Lowry's method or the microburet method,
      saccharide-positive by the phenol-sulfuric acid method or anthrone-sulfuric acid method;
   (7) Biological activities:
      cytotoxic on L 929 cell,
      substantially not growth-inhibitive on KB cell,
      substantially free from interferon activity;
   (8) Stability in aqueous solution:
      stable up to 60° C. when incubated at pH 7.2 for 30 minutes,
      stable in the pH range of 4.0–11.0 when incubated at 4° C. for 16 hours; and
   (9) Stability on cryopreservation:
      stable at −10° C. over a period of one month or longer.

2. LK 2, whenever produced by a process comprising:
   exposing human cells capable of producing LK 2 to an LK 2 inducer; and
   recovering a product consisting essentially of the accumulated LK 2.

3. The LK 2 of claim 2, wherein the human cells capable of producing LK 2 are human leukocytes or human lymphocytes.

4. The LK 2 of claim 2, wherein the human cells capable of producing LK 2 are lymphoblastoid cells.

5. The LK 2 of claim 2, wherein the human cells capable of producing LK 2 are a member selected from the group consisting of Namalwa cells (ATCC CRL 1432), BALL-1 cells, TALL-1 cells, NALL-1 cells, M-7002 cells, B-7101 cells, JBL cells, EBV-Sa cells, EBV-Wa cells, EBV-HO cells, MOLT-3 cells, (ATCC CRL 1552), CCRF-SB cells (ATCC CRL 120), CCRF-CEM cells (ATCC CCL 119), BALM 2 cells, DND-41 cells, and Mono-1 cells.

6. The LK 2 of claim 2, wherein said exposing step is carried out in vitro.

7. The LK 2 of claim 2, wherein said exposing step is carried out in vivo.

8. The LK 2 of claim 2, wherein the LK 2 inducer is a member selected from the group consisting of interferon-α inducer, interferon-γ inducer, and mixtures thereof.

9. The LK 2 of claim 2, wherein said human cells capable of producing LK 2 are obtained by proliferating a human cell capable of producing LK 2, and wherein said exposing step takes place under conditions sufficient to accumulate a substantial amount of LK 2.

10. The LK 2 of claim 9, wherein the human cells capable of producing LK 2 are proliferated in vitro.

11. The LK 2 of claim 9, wherein the human cells capable of producing LK 2 are proliferated in vivo.

12. The LK 2 of claim 2, wherein the human cells capable of producing LK 2 are obtained by:
   transplanting human cells capable of producing LK 2 to a non-human warm-blooded animal;

feeding the animal to allow the human cells to utilize the nutrient body fluid of the animal for its proliferation; and extracting and disaggregating the resultant tumor formed in the animal.

13. The LK 2 of claim 12, wherein the non-human warm-blooded animal is a fowl or a mammal.

14. The LK 2 of claim 12, wherein the non-human warm-blooded animal is immunodeficient or immunosuppressed.

15. The LK 2 of claim 2, wherein the human cells capable of producing LK 2 are obtained by:

suspending human cells capable of producing LK 2 in a diffusion chamber in which the nutrient body fluid of a non-human warm-blooded animal is supplied to the human cells;

embedding or placing said chamber in or on a non-human warm-blooded animal in a manner such that the nutrient body fluid of the animal is supplied to the human cells within said chamber;

feeding the animal to allow the human cells to utilize the nutrient body fluid for their proliferation; and collecting the proliferated human cells from the chamber.

16. The LK 2 of claim 15, wherein the non-human warm-blooded animal is a fowl or a mammal.

17. The LK 2 of claim 15, wherein said diffusion chamber is equipped with one or more membrane filters, hollow fibers or ultra-filters having a nominal pore size of $10^{-7}$–$10^{-5}$ m.

18. A lymphokine consisting essentially of LK 2.

19. A pharamaceutical composition comprising a pharmaceutically acceptable carrier and LK 2 in accordance with claim 18 in an amount effective to enhance the antioncotic activity of an additional chemotherapeutic agent.

20. In an antioncotic pharmaceutical composition comprising an effective amount of a chemotherapeutic agent and a pharmaceutically acceptable carrier, the improvement whereby the activity of said chemotherapeutic agent is enhanced wherein said composition further includes LK 2 in accordance with claim 52 in an amount effective to enhance the antioncotic activity of said chemotherapeutic agent.

21. The composition in accordance with claim 20, wherein said chemotherapeutic agent is a member selected from the group consisting of alkylating agent, metabolic antagonist, antioncotic antibiotic, alkaloid, and mixtures. thereof.

22. A pharmaceutical composition comprising a pharmaceutically acceptable carrier and LK 2 in accordance with claim 18 in an antioncontically effective amount.

23. The composition in accordance with claim 22, which contains LK 2 at least 5 units/g.

24. The composition in accordance with claim 22, in the form of an injection fluid, collyrium, ointment, suppository or collunarium.

25. A substantially-pure LK 2.

26. The LK 2 in accordance with claim 25, having a specific activity of at least $10^6$ units/mg protein.

* * * * *